(12) United States Patent
Herold et al.

(10) Patent No.: US 7,754,915 B2
(45) Date of Patent: *Jul. 13, 2010

(54) PROCESS FOR PREPARING ISOCYANATES IN THE GAS PHASE

(75) Inventors: Heiko Herold, Neuss (DE); Volker Michele, Köln (DE); Werner König, Leverkusen (DE)

(73) Assignee: Bayer MaterialScience AG, Leverkusen (DE)

( * ) Notice: Subject to any disclaimer, the term of this patent is extended or adjusted under 35 U.S.C. 154(b) by 543 days.

This patent is subject to a terminal disclaimer.

(21) Appl. No.: 10/969,704

(22) Filed: Oct. 20, 2004

(65) Prior Publication Data

US 2005/0113601 A1    May 26, 2005

(30) Foreign Application Priority Data

Oct. 23, 2003 (DE) ................. 103 49 504

(51) Int. Cl.
*C07C 291/00* (2006.01)
(52) U.S. Cl. .................................... 560/347
(58) Field of Classification Search ......... 560/330, 560/336, 338, 347
See application file for complete search history.

(56) References Cited

U.S. PATENT DOCUMENTS

| 4,289,732 | A |  | 9/1981 | Bauer et al. ............. 422/224 |
|---|---|---|---|---|
| 4,419,295 | A |  | 12/1983 | Hennig et al. ......... 260/453 PH |
| 4,847,408 | A | * | 7/1989 | Frosch et al. ............ 560/347 |
| 5,449,818 | A |  | 9/1995 | Biskup et al. ............ 560/347 |
| 5,633,396 | A |  | 5/1997 | Bischof et al. ........... 560/347 |
| 6,803,482 | B2 | * | 10/2004 | Jenne et al. ............. 560/347 |
| 6,838,578 | B2 | * | 1/2005 | Leimkuhler et al. ...... 560/330 |
| 2004/0167354 | A1 |  | 8/2004 | Biskup et al. ............ 560/336 |
| 2004/0192959 | A1 | * | 9/2004 | Woelfert et al. .......... 560/347 |

FOREIGN PATENT DOCUMENTS

GB    1 238 669    7/1971

OTHER PUBLICATIONS

Perry's Chemical Engineers' Handbook (7th Edition) Edited by: Perry, R.H.; Green, D.W. © 1997 McGraw-Hill, p. 18-32.*
Chemie-Ing. Techn. 44, (month unavailable) 1972, pp. 1051-1055, K.H. Hartung et al, "Beschleunigung der turbulenten Mischung in Rohren" (see p. 1055-figure 10).

* cited by examiner

*Primary Examiner*—Karl J Puttlitz
(74) *Attorney, Agent, or Firm*—Lyndanne M. Whalen; Noland J. Cheung

(57) ABSTRACT

A process for preparing isocyanates in the gas phase, in which the mixing of the reactants and thus the reaction conditions are significantly improved by means of hydrodynamic measures such as increasing the turbulence of the feed stream in the central nozzle. As a consequence, the necessary residence time in the reactor and thus the length of the reactor are reduced and the formation of polymeric by-products which lead to caking in the reactor and a shortening of the operating period of the reactors is avoided.

14 Claims, 3 Drawing Sheets

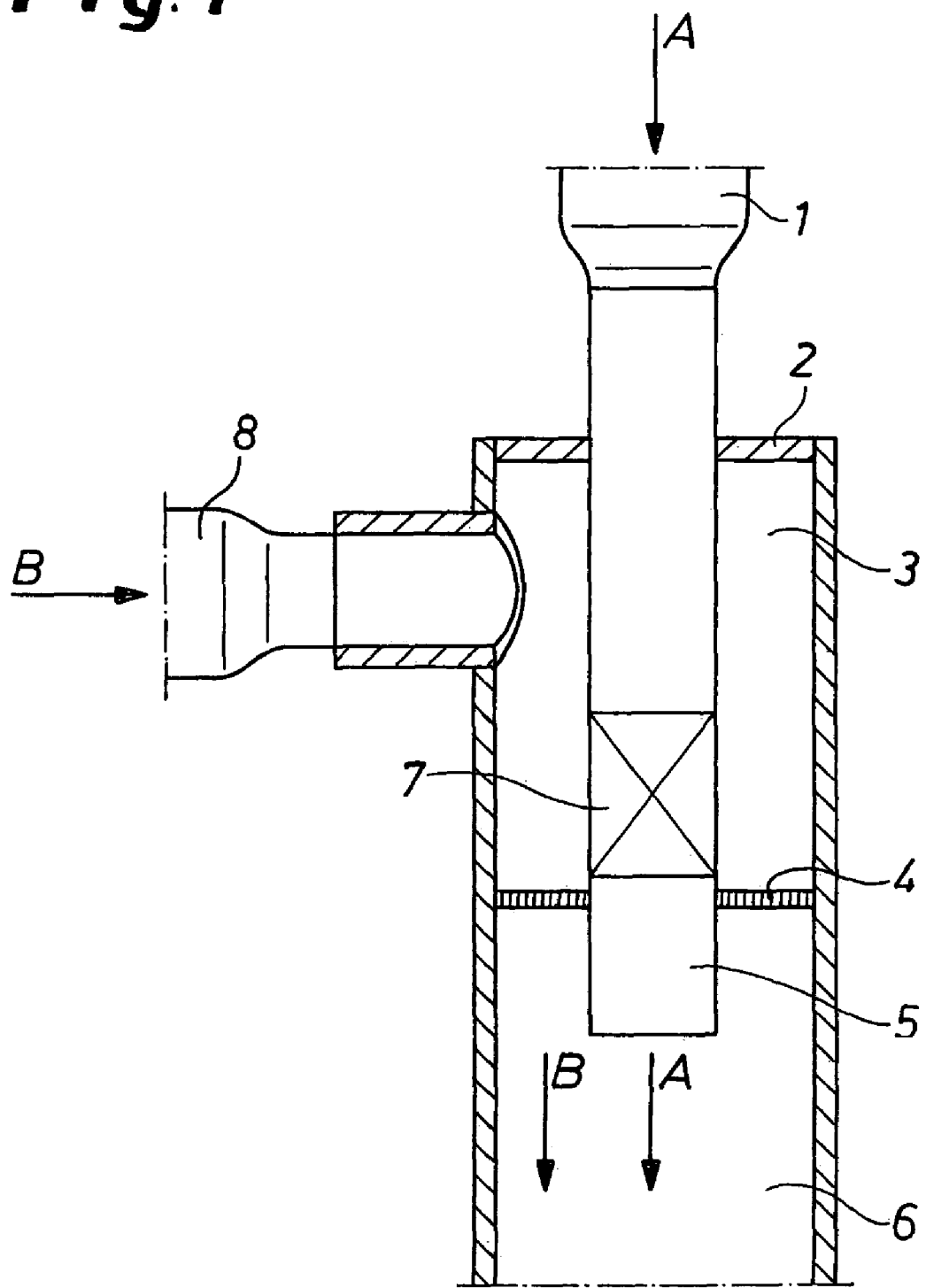

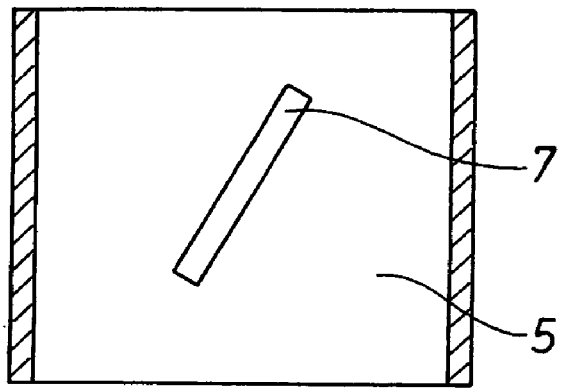
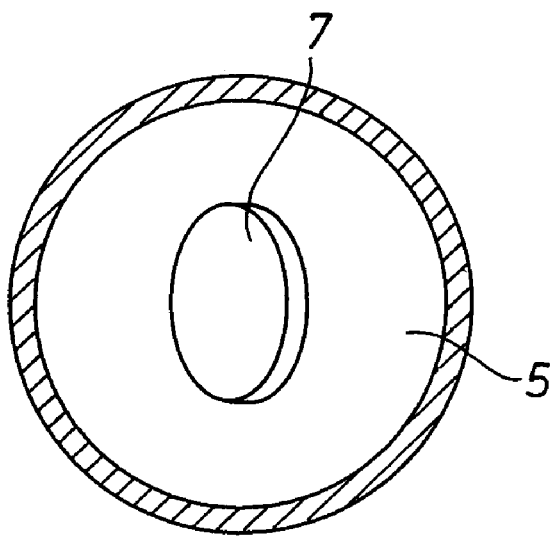

PROCESS FOR PREPARING ISOCYANATES IN THE GAS PHASE

CROSS REFERENCE TO RELATED PATENT APPLICATION

The present patent application claims the right of priority under 35 U.S.C. §119 (a)-(d) of German Patent Application No. 103 49 504.5, filed Oct. 23, 2003.

BACKGROUND OF THE INVENTION

1. Field of the Invention

The invention is directed to a process for preparing isocyanates in the gas phase and in particular to improved mixing of the reactants used in such a process.

2. Description of the Prior Art

EP-A 0 289 840 describes a process for preparing (cyclo)aliphatic diisocyanates by phosgenation of the corresponding, gaseous (cyclo)aliphatic diamines at from 200° C. to 600° C. Phosgene is introduced in a stoichiometric excess. The superheated streams of, firstly, gaseous (cyclo)aliphatic diamine or (cyclo)aliphatic diamine/inert gas mixture and, secondly, phosgene are fed continuously into a cylindrical reaction chamber, mixed with one another there and reacted. The exothermic phosgenation reaction is carried out with turbulent flow being maintained.

Gaseous starting materials are frequently reacted in tube reactors. In the case of the jet mixer principle (Chemie-Ing.-Techn. 44 (1972) p. 1055, FIG. 10), two feed streams A and B are fed into the reactor, with feed stream A being introduced via a central nozzle and feed stream B being introduced via an annular space between the central nozzle and the wall of the tube reactor. The flow velocity of the feed stream A is high compared to the flow velocity of the feed stream B. As a result, the mixing of the reactants and consequently the reaction between them occur in the tube reactor. This way of carrying out the reaction has achieved industrial importance in the preparation of aromatic diisocyanates by phosgenation of aromatic diamines in the gase phase (e.g. EP-A-0 570 799).

The known processes require very long reactors since mixing occurs slowly without additional measures.

A consequence of the slow mixing of the reactants is the formation of polymeric by-products which lead to caking and even blockages in the reactor and thus shorten the operating period of the reactors. In addition, the greater lengths of the reactors lead to increased capital costs.

It is therefore an object of the invention to find a process for preparing (cyclo)aliphatic and aromatic diisocyanates by phosgenation of corresponding (cyclo)aliphatic and aromatic diamines in the gas phase at high temperatures, in which mixing of the reactants occurs significantly more quickly than in the processes known hitherto.

SUMMARY OF THE INVENTION

The present invention relates to a process for preparing isocyanates in the gas phase, in which the mixing of the reactants is significantly improved by means of improved reaction conditions in tube reactors using hydrodynamic measures such as increasing the turbulence. As a consequence, the necessary residence time of the reactants in the reactor and thus the length of reactor needed are shortened and the formation of polymeric by-products which lead to caking in the reactor and a shortening of the operating period of the reactors is avoided.

Thus, the present invention is directed to a process for preparing diisocyanates and triisocyanates of the general formula (I)

$$R(NCO)_n \qquad (I)$$

where
R is a (cyclo)aliphatic or aromatic hydrocarbon radical having up to 15 carbon atoms, with the proviso that at least two carbon atoms are present between two NCO groups and
n is 2 or 3, The inventive process includes phosgenating diamines and/or triamines of the general formula (II) in the gas phase $$R(NH_2)_n \qquad (II)$$

where
R is a (cyclo)aliphatic or aromatic hydrocarbon radical having up to 15 carbon atoms, with the proviso that at least two carbon atoms are present between two amino groups and
n is 2 or 3,
where the phosgenating is carried out in a tube reactor having a central nozzle and an annular space between the central nozzle and a wall of the tube reactor, wherein turbulence is generated in the central nozzle and in which a feed stream containing the diamines and/or triamines is fed into the tube reactor via the central nozzle and a phosgene-containing feed stream is fed into the tube reactor via the annular space.

BRIEF DESCRIPTION OF THE DRAWINGS

FIG. 1 shows a partial elevation view of a tube reactor according to the invention;

FIG. 2A shows a side elevation view of an oblique plate as a turbulence generator for the tube reactor in FIG. 1;

FIG. 2B shows a plan view of an oblique plate as a turbulence generator for the tube reactor in FIG. 1.

DETAILED DESCRIPTION OF THE INVENTION

Figure 3:
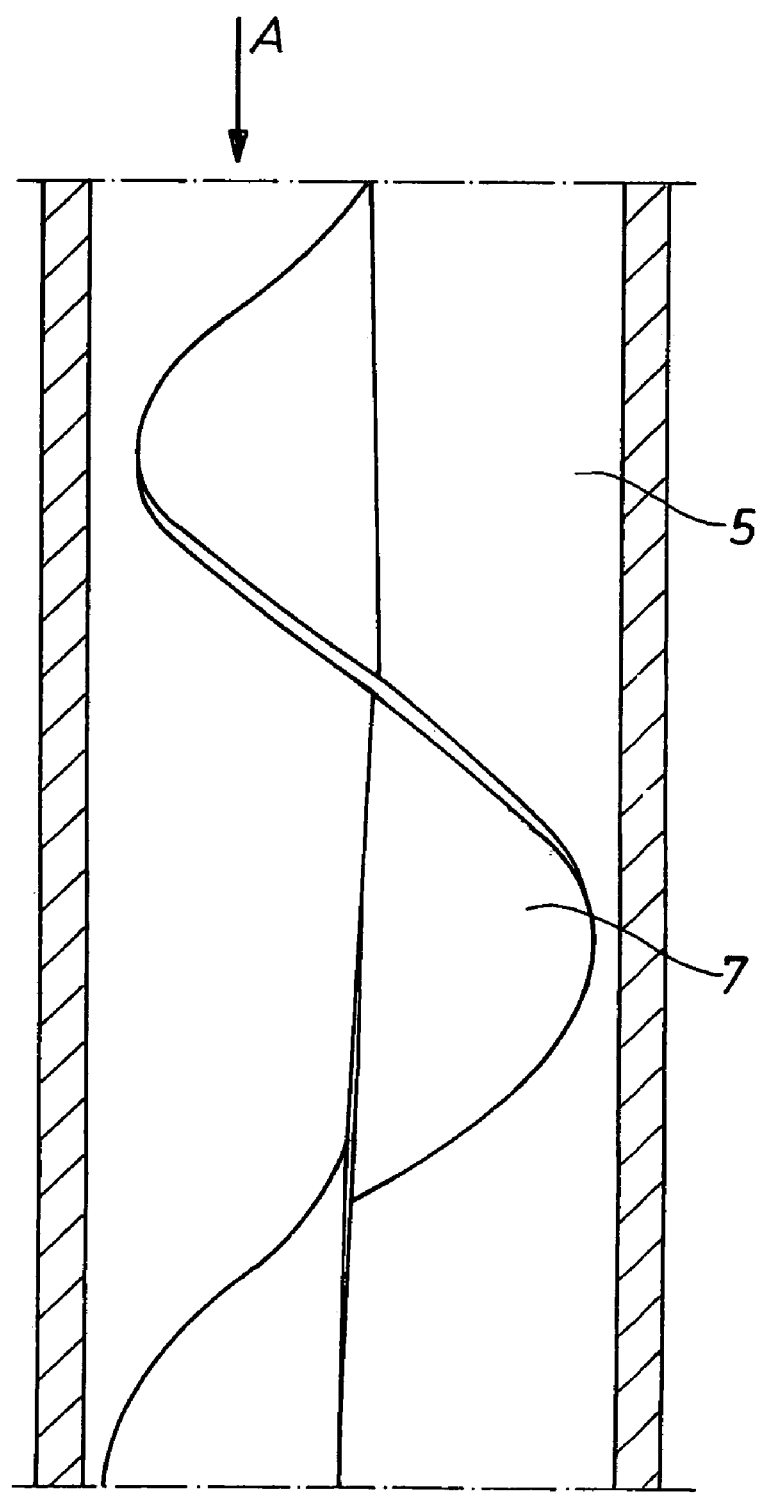
FIG. 3 shows a helical element that can be used as a turbulence generator in the tube reactor of the present invention.

Other than in the operating examples, or where otherwise indicated, all numbers or expressions referring to quantities of ingredients, reaction conditions, etc. used in the specification and claims are to be understood as modified in all instances by the term "about."

It has now surprisingly been found that increasing the turbulence of the feed stream in the central nozzle has a positive influence on the mixing of the reactants and thus on the gas-phase reaction as a whole. As a consequence of the better mixing, the tendency for by-products to be formed decreases and the necessary residence time and thus reactor length drop significantly. Thus, the disadvantages of the processes of the prior art can be significantly reduced when the feed streams are subjected to the novel measures described in more detail below.

The invention provides a process for preparing diisocyanates and triisocyanates of the general formula (I)

$$R(NCO)_n \qquad (I)$$

where
R is a (cyclo)aliphatic or aromatic hydrocarbon radical having up to 15 carbon atoms, preferably from 4 to 13 carbon atoms, with the proviso that at least two carbon atoms are present between two NCO groups and
n is 2 or 3, by phosgenation of the corresponding diamines and/or triamines of the general formula (II) in the gas phase $$R(NH_2)_n \quad (II)$$

where
R is a (cyclo)aliphatic or aromatic hydrocarbon radical having up to 15, preferably from 4 to 13, carbon atoms, with the proviso that at least two carbon atoms are present between two amino groups and
n is 2 or 3, characterized in that the phosgenation is carried out in a tube reactor having a central nozzle and an annular space between the central nozzle and the wall of the tube reactor, with the central nozzle being centred in the tube reactor and the central nozzle being connected to an inlet for one of the feed streams and the inlet for a second feed stream being located in the annular space and with turbulence being generated in the central nozzle, in which the feed stream containing the diamines and/or triamines is fed into the tube reactor via the central nozzle and the phosgene-containing feed stream is fed into the tube reactor via the annular space. The degree of turbulence of the stream flowing through the central nozzle is preferably increased by means of internal elements.

In an alternative embodiment of the process of the invention, the feed stream containing the diamines and/or triamines and the phosgene-containing feed stream are interchanged so that the feed stream containing the diamines and/or triamines is fed into the tube reactor via the annular space and the phosgene-containing feed stream is fed into the tube reactor via the central nozzle.

Preference is given to using one or more round or annular plates installed obliquely in the stream or a helix as turbulence-increasing internal elements in the central nozzle.

The task of the oblique plate or the combination of a plurality of oblique plates is to increase the degree of turbulence in the central nozzle.

The task of the helix is to increase the degree of turbulence in the stream in the central nozzle and to twist the stream in order to utilize centrifugal effects to aid mixing of inner and outer streams.

The process of the invention makes it possible to shorten the mixing distance of feed streams fed in via the annular space and via the central nozzle by at least 50% compared to the comparative value without turbulence-generating internals.

In the process of the invention, diisocyanates and/or triisocyanates are prepared from the corresponding diamines and/or triamines.

Preference is given to preparing diisocyanates by phosgenation of the corresponding diamines in the process of the invention.

As triisocyanate of the formula (I), 1,8-diisocyanato-4-(isocyanatomethyl)octane, also known as triisocyanatononane (TIN), is preferably prepared in the process of the invention.

Typical examples of suitable aliphatic diamines are mentioned in, for example, EP-A 0 289 840, and typical examples of suitable aliphatic triamines are mentioned in, for example, EP-A 749 958. These diamines are suitable for preparing the corresponding diisocyanates or triisocyanates by the process of the invention.

Preference is given to isophoronediamine (IPDA), hexamethylenediamine (HDA) and bis(p-aminocyclohexyl)methane.

Typical examples of suitable aromatic diamines are the pure isomers or the isomer mixtures of diaminobenzene, diaminotoluene, diaminodimethylbenzene, diaminonaphthalene and diaminodiphenylmethane; preference is given to 2,4-/2,6-toluenediamine mixtures having isomer ratios of 80/20 and 65/35 or the pure 2,4-toluenediamine isomer.

As triamine, preference is given to using 1,8-diamino-4-(aminomethyl)octane, also known as triaminononane.

The starting amines of the formula (II) are fed into the reactor in gaseous form and are, if appropriate, vaporized and preferably heated to from 200° C. to 600° C., particularly preferably from 250° C. to 450° C., before carrying out the process of the invention and are fed, if appropriate after dilution with an inert gas such as $N_2$, Ne, He, Ar or with the vapour of an inert solvent, into the reactor. The phosgene is fed into the tube reactor in a stoichiometric excess and at from 200° C. to 600° C. When using aliphatic diamines, the molar excess of phosgene based on one amino group is preferably from 25% to 250%, and when using aliphatic triamines is preferably from 50% to 350%. When aromatic diamines are used, the molar excess of phosgene based on an amino group is preferably from 150% to 300%.

In the following, the invention is illustrated by way of example with the aid of FIG. 1. The feed stream A (diamine and/or triamine) flows via the inlet 1 and the central nozzle 5 into the tube reactor 6.

The central nozzle 5 is held in position by the lid 2 and the holder 4 and is centred on the axis of rotation of the tube reactor 6. One or more turbulence-generating elements 7 are located in the central nozzle.

The feed stream B (phosgene) flows through the inlet 8 into the annular space 3 of the tube reactor 6.

FIGS. 2A and 2B show a preferred oblique plate as turbulence generator 7.

FIG. 3 shows a preferred helical element 8 as turbulence generator 7.

EXAMPLE

Starting materials A and B are fed, in each case as a gas, into a model tube reactor as shown in FIG. 1 (length: 2000 mm, internal diameter of the outer tube: 172 mm, internal diameter of the inner tube: 54 mm), with the gas of the inner stream (starting material A) being seeded by addition of aerosols.

The experiment is firstly carried out according to the invention using a helix as shown in FIG. 3 as turbulence-generating element in the central nozzle; the length of the helix was 135 mm, its diameter was 54 mm, and the twist was 360°.

Secondly, the experiment is carried out without turbulence-generating internals in the central nozzle for comparison.

Mixing of inner and outer streams downstream of the mouth of the central nozzle can then be assessed visually on the basis of the radial distribution of the aerosols of the inner stream. Complete mixing of inner and outer streams is regarded as having been achieved when the aerosols from the inner stream have reached the wall of the outer tube. The axial length of the path in the tube reactor from the mouth of the central nozzle to this point will hereinafter be referred to as the mixing distance.

In the experiment carried out as comparative example, the mixing distance was 1200 mm. In the experiment carried out according to the invention using the helix as turbulence-generating internal element, the mixing distance was only 500 mm. The mixing distance in the process of the invention is thus only 42% of the original distance.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing diisocyanates and triisocyanates of the general formula (I)

where
R is a (cyclo)aliphatic or aromatic hydrocarbon radical having up to 15 carbon atoms, with the proviso that at least two carbon atoms are present between two NCO groups and
n is 2 or 3,
comprising phosgenating diamines and/or triamines of the general formula (II) in the gas phase

where
R is a (cyclo)aliphatic or aromatic hydrocarbon radical having up to 15 carbon atoms, with the proviso that at least two carbon atoms are present between two amino groups and
n is 2 or 3,
wherein the phosgenating is carried out in a tube reactor having a central nozzle and an annular space between the central nozzle and a wall of the tube reactor, wherein turbulence is generated in the central nozzle and in which a feed stream containing the diamines and/or triamines is fed into the tube reactor via the central nozzle and a phosgene-containing feed stream is fed into the tube reactor via the annular space wherein round or angular oblique plates, or a helix, are used as turbulence-generating elements.

2. The process according to claim 1, in which the feed stream containing the diamines and/or triamines and the phosgene-containing feed stream are interchanged so that the feed stream containing the diamines and/or triamines is fed into the tube reactor via the annular space and the phosgene-containing feed stream is fed into the tube reactor via the central nozzle.

3. The process according to claim 1, wherein the turbulence of the stream conveyed through the central nozzle is increased by means of one or more turbulence-generating internal elements.

4. The process according to claim 1, wherein diisocyanates are prepared by phosgenation of the corresponding diamines.

5. The process according to claim 1, wherein gaseous (cyclo)aliphatic and/or aromatic diamines at from 200° C. to 600° C. are fed into the tube reactor via the central nozzle and phosgene is fed into the tube reactor in a stoichiometric excess at from 200° C. to 600° C. via the annular space.

6. The process according to claim 1, wherein isophoronediamine (IPDA) or hexamethylenediamine (HAD) or bis(p-aminocyclohexyl)methane are used as the diamines.

7. The process according to claim 1, wherein 2,4-/2,6-toluenediamine mixtures having isomer ratios of 80/20 to 65/35 or the pure 2,4-toluenediamine isomer are used as the diamines.

8. The process according to claim 1, wherein triisocyanatononane is prepared.

9. The process according to claim 1, wherein R is from 4 to 13 carbon atoms.

10. The process according to claim 3, wherein diisocyanates are prepared by phosgenation of the corresponding diamines.

11. The process according to claim 3, wherein gaseous (cyclo)aliphatic and/or aromatic diamines at from 200° C. to 600° C. are fed into the tube reactor via the central nozzle and phosgene is fed into the tube reactor in a stoichiometric excess at from 200° C. to 600° C. via the annular space.

12. The process according to claim 3, wherein isophoronediamine (IPDA) or hexamethylenediamine (HAD) or bis (p-aminocyclohexyl)methane are used as the diamines.

13. The process according to claim 3, wherein 2,4-/2,6-toluenediamine mixtures having isomer ratios of 80/20 to 65/35 or the pure 2,4-toluenediamine isomer are used as the diamines.

14. The process according to claim 3, wherein triisocyanatononane is prepared.

* * * * *